US006447464B1

(12) United States Patent
Dunlevy et al.

(10) Patent No.: US 6,447,464 B1
(45) **Date of Patent: *Sep. 10, 2002**

(54) THERAPY DEVICE FOR UPPER EXTREMITY DYSFUNCTION

(75) Inventors: Mindy Dunlevy; Michael Dunlevy, both of Winter Springs, FL (US)

(73) Assignee: Lifespan Therapy Services, Inc., Orlando, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/405,673

(22) Filed: Sep. 24, 1999

(51) Int. Cl.[7] .............................. A61H 1/00; A61F 5/00; A41D 19/00

(52) U.S. Cl. .............................. 601/40; 602/5; 602/21; 2/159; 2/160; 482/44

(58) Field of Search .............................. D30/134, 135; 182/3; 280/290; 54/6.1; 602/21, 22, 64; 2/159–161.8

(56) References Cited

U.S. PATENT DOCUMENTS

| | | | | |
|---|---|---|---|---|
| 835,968 A | | 11/1906 | Mennes | 586/221.5 |
| 3,604,307 A | | 9/1971 | Vonno | 84/465 |
| 3,655,185 A | | 4/1972 | Kane | 272/82 |
| 3,747,593 A | | 7/1973 | Taylor | 128/26 |
| 4,220,334 A | | 9/1980 | Kanamoto et al. | 272/67 |
| 4,273,215 A | * | 6/1981 | Leggett | 182/3 |
| 4,858,912 A | | 8/1989 | Boyd | 272/67 |
| 4,960,114 A | | 10/1990 | Dale | 128/87 R |
| 5,141,478 A | | 8/1992 | Upper | 482/44 |
| 5,191,903 A | | 3/1993 | Donohue | 128/879 |

(List continued on next page.)

OTHER PUBLICATIONS

Perception of Space of Adult Heliplegic Patients, Jean Ayre, Archives of Physical Medicine, vol. 43, pp. 552–555, 1962.

(List continued on next page.)

*Primary Examiner*—Kim M. Lewis
(74) *Attorney, Agent, or Firm*—Brian S. Steinberger; Law Offices of Brian S. Steinberger, P. A.

(57) ABSTRACT

Gloves and harnesses for allowing patients to do rehabilitation and reeducation exercises. A first version allows a therapist to exercise a second person's hand(s) including their fingers, wrists, and arms by overlying the palm(s) of the therapist's hand(s) over the dorsum back of the patient's hand(s). The therapist wears a glove(s) having fasteners extending from the sides of the pinkie, fourth finger, middle finger, index finger and thumb, and a wrist portion, for wrapping about the corresponding fingers and wrist of the patients hand(s). The fasteners can include hook and loop straps, and self adhesive straps, and the like. A second version is a grasp assistance glove used by a single person where a patient wears a glove(s) having fastener straps extending outward from the tips of the pinkie, fourth finger, middle finger, index finger, and thumb portions, and a fastener attached to the palm portion of the glove. An object such as a bar is grasped by the patient's gloved hand by having the straps of the fingers attached to the palm fasteners, with the fasteners being similar to those of the first version. A third version has a safety harness that can be used with or without the hand over hand glove system. The harness has a first belt section for wrapping about the waist of the therapist, and a second belt section for wrapping about both the waist and between the legs of the patient. The first and second belt sections can attach to the therapist and patient by hook and loop fasteners, self adhesive tape, buckle clasps and the like. The harness is useful to increase safety and to decrease a patient's fear of falling while the patient is performing rehabilitation and reeducation exercises.

17 Claims, 16 Drawing Sheets

U.S. PATENT DOCUMENTS

| | | | | | |
|---|---|---|---|---|---|
| 5,397,298 | A | * | 3/1995 | Mazza et al. | 602/75 |
| 5,435,013 | A | * | 7/1995 | Davis | 2/161.1 |
| 5,447,490 | A | | 9/1995 | Fula et al. | 601/40 |
| 5,711,747 | A | | 1/1998 | Steinback | 482/124 |
| 5,759,165 | A | | 6/1998 | Malewicz | 602/21 |
| 5,769,758 | A | | 6/1998 | Sarkinen | 482/44 |
| 5,800,561 | A | | 9/1998 | Rodriguez | 623/26 |

OTHER PUBLICATIONS

Man's JSearch for Meaning, Viktor Frankl, Washington Square Press, pp. 96–97, 1985.

An Investigation of Body Scheme in Adults with Cerebral Vascular Accident, J. MacDonald, American Journal of Occupational Therapy, vol. 14, pp. 75–79, 1960.

Return to Ithaca, Brabara Newborn, Element Books Unlimited, pp. 98–99, 1997.

Occupational Therapy Practice Skills for Physical Dysfunction (third edition), Loraine Padretti and Barbara Zoltan, C.V. Mosby Company, p. 335, 1990.

The Adult Stroke Patient (second edition), Barbara Zoltan, et al., Slack Incorporated, pp. iv, 53 and 179, 1990.

* cited by examiner

THERAPY DEVICE FOR UPPER EXTREMITY DYSFUNCTION

This invention relates to therapy devices, and in particular to devices that enable persons with upper extremity dysfunction's to exercise upper body parts such as hands and arms through rehabilitation and reeducation exercises.

BACKGROUND AND PRIOR ART

An increasing percentage of the United States population suffers from motor planning dysfunction's and abnormal muscle tones as a result of various etiologies such as but not limited to Cerebral Vascular Accidents(CVA), head injuries and cerebral palsy. For example, there are approximately 500,000 new victims of Cerebral Vascular Accidents(CVA) annually in the United States. Additionally, at any given time there are two million persons who have survived strokes. Approximately seventy five percent of these affected persons will be rehabilitated to some degree of independence. Approximately sixty to seventy percent of these individuals can expect to become ambulatory. However, only approximately thirty to forty percent are expected to regain significant functional return of the affected upper extremity. See Zoltan et al, The Adult Stroke Patient, The Adult Stoke Patient, 2$^{nd}$ Edition, New Jersey, Slack Inc., pages iv, 53, 179. Clearly, there is a need to improve the rehab success rates for post-stroke patients that are increasingly becoming a larger part of the U.S. population.

One of the most devastating effects of stroke cases are their economic impacts. The annual cost of strokes in the United States is approximately thirty billion dollars! This includes approximately seventeen billion in direct medical costs and approximately thirteen billion in loss of productivity. See Newborn, Barbara, Return to Ithacca, USA, Element Books Unlimited, 1997, pages 98–99. As a nation, the United States is putting a great deal of money toward relatively unsuccessful rehabilitation systems without ever questioning how these systems can be improved.

Key stumbling blocks exist for stroke rehabilitation that are being overlooked during actual rehabilitation treatments due to the fact that there are no particularly effective methods available that can take place during the limited treatment times available. For instance, treatment is generally focused on the physical recovery and not toward the underlying sensory issues that are necessary components of motor functions. For example, "the body scheme is one of the essential elements involved in purposeful motor behavior." See MacDonald, J., An Investigation of Body Scheme In Adults With Cerebral Vascular Accident, American Journal Of Occupational Therapy, 1960, pages 75–79. By definition, a body scheme covers "a postural model one has of himself, having to do with how one perceives the position of the body and the relationship of body parts. It is believed to be the basis of all movement . . . " See Zoltan et al, The Adult Stroke Patient, The Adult Stoke Patient, 2$^{nd}$ Edition, New Jersey, Slack Inc., pages iv, 53, 179.

It is a fact that the patient must be able to orient themselves to the relationship of their body parts to one another to create purposeful movement. It has also been a proven result of research studies that body scheme disorders were typical of CVA patients irrespective of whether the patient has right or left hemisphere damage. See MacDonald, J., An Investigation of Body Scheme In Adults With Cerebral Vascular Accident, American Journal Of Occupational Therapy, 1960, pages 75–79. This being the case, body scheme disorders need to be aggressively targeted as a part of treatment before functional motor recovery can be expected to return.

Another often overlooked key to motor recovery is the importance of receiving accurate sensory input on a consistent activity-related basis. Without this input, the body is not provided adequate information to interpret in order for accurate motor output to occur in this afferent-efferent system.

Studies have proven the following about the importance of sensation to overall upper extremity functioning: (1) sensation is critical to movement; (2) without sensation a limb becomes essentially useless; (3) preservation of cutaneous sensation in the hand is indispensable for motor function of the upper limb; and (4) movements of the upper limb, particularly grasp function, are directed by contractual stimuli. See Padretti & Zoltan, Occupational Therapy Practice Skills For Physical Dysfunction, 3$^{rd}$ edition, St. Louis, C. V. Mosby Co., 1990, page 335.

The information from the hand guides the fingers around objects for grasp. Alternatively, information from the hand guides the movement of an object in the hand. Sensory information is crucial for precise movements. The fingers and thumb need tactile information to learn how to move the fingers and thumb together, and how to move the fingers and thumb independent from one another. Gripping and grasping manipulations are also dictated by tactile information entering the central nervous system and being transferred to the hand musculature. Once the hand grips and grasps the object, the tactile system is the dominant force in developing the grip and the grasp manipulations. Information from the tactile system is needed to regulate the force of the grasp and to control the slippage of objects. Therefore, any period of time that the hemiplegic side is not incorporated into daily activities, the body is deprived of essential input needed to interpret the environment in order to form an appropriate motor response. Feedback on the success of the movement is provided by effectiveness of task completion, which is required to reinforce this closed system response.

Various techniques have been proposed over the years that could be useful for rehabilitation and reeducation exercises. See for example, U.S. Pat. No. : 835,968 to Mennes; U.S. Pat. No. 3,604,307 to Vono; U.S. Pat. No. 3,655,185 to Kane; U.S. Pat. No. 3,747,593 to Taylor; U.S. Pat. No. 4,220,334 to Kanamoto et al.; U.S. Pat. No. 4,858,912 to Boyd; U.S. Pat. No. 4,960,114 to Dale; U.S. Pat. No. 5,141,478 to Upper; U.S. Pat. No. 5,191,903 to Donohue; U.S. Pat. No. 5,447,490 to Fula et al.; U.S. Pat. No. 5,711,747 to Steinback; U.S. Pat. No. 5,759,165 to Malewicz; U.S. Pat. No. 5,769,758 to Sarkinen; and U.S. Pat. No. 5,800,561 to Rodriguez. However, none of these devices provide an adequate therapeutic tool that allows for controlled hand over hand assistance that would be required for neuralgic retraining of the hemiplegic extremity.

SUMMARY OF THE INVENTION

The first objective of the present invention is to provide a modality to allow one person to practice upper body therapeutic exercises and activities to another person using controlled hand over hand assistance.

The second object of this invention is to provide a grasp assistance device to allow a single person to practice upper body neural muscular rehabilitation and reeducation exercises.

The third object of this invention is to provide therapy safety harness devices to provide safety and to decrease a patients fear of falling while providing hand over hand while doing upper body neural muscular rehabilitation and reeducation exercises to another person's upper body.

A first preferred embodiment of the invention is for a hand over hand assistance glove where a palm surface of a therapist's hand lays in symmetry on top of the dorsum portion of the patient's affected hand. For example, the right hand of the therapist on the right hand of the patient, and the left hand of the therapist on the left hand of the patient. The therapist wears a glove having one inch by six inch strips of adhesive material extending from the sides of each finger and thumb to securely wrap around the patient's fingers. Once the device is in place, the therapist can guide the patient through movement patterns. The therapist's hand movements can control the paitient's hand movements including reach, gross/refined grasp, fine pinch, in-hand manipulations, opposition type movements, functional object manipulations, and the like, to perform functional motor activities while allowing the patient to receive real and not simulated, sensory input to the hand.

A second preferred embodiment is a grasp assistance glove that allows patients to maintain a functional grasp for assisted activities and positioning. The patient can independently perform various exercises as well as positioning their affected upper extremity in edema controlling/anti-synergy positions. The palmer side of the glove can be covered with hook and loop(Velcro®) type fasteners, with four inch long straps extending from each finger and thumb. The patient's lingers wrap about the object to be grasped(such as a bar) by attaching the fasteners extending outward from the fingers of the glove to the mating fasteners at the wrist area of the glove. The thumb straps wraps around to affix to hook and loop fasteners on backs of fingers.

The third embodiment includes a therapy harness that is used to increase safety and to decrease patient fear of falling while performing standing activities. As fear of falling has been noted to increase muscle tone, this will not only provide a safer therapy session but also help normalize movements to get the maximum benefit of treatment. This embodiment will allow the therapist/aide to perform activities with the first embodiment hand over hand assistance glove without compromising safety. The belt harness allows the therapist/aide to use their own body to support the patient safely if balance and stability is compromised. The therapist wears a harness belt that can be made of a heavy canvass material with a sturdy metal type tooth clasp which securely affixes to an identical adjoining belt of the same material with an extra strap to be worn between the patient's legs for harness style support. Alternatively, the harness can be secured to a stationary object such as a support pillar, a door, and the like.

Further objects and advantages of this invention will be apparent from the following detailed description of a presently preferred embodiment which is illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

First Embodiment

Figure 1A:
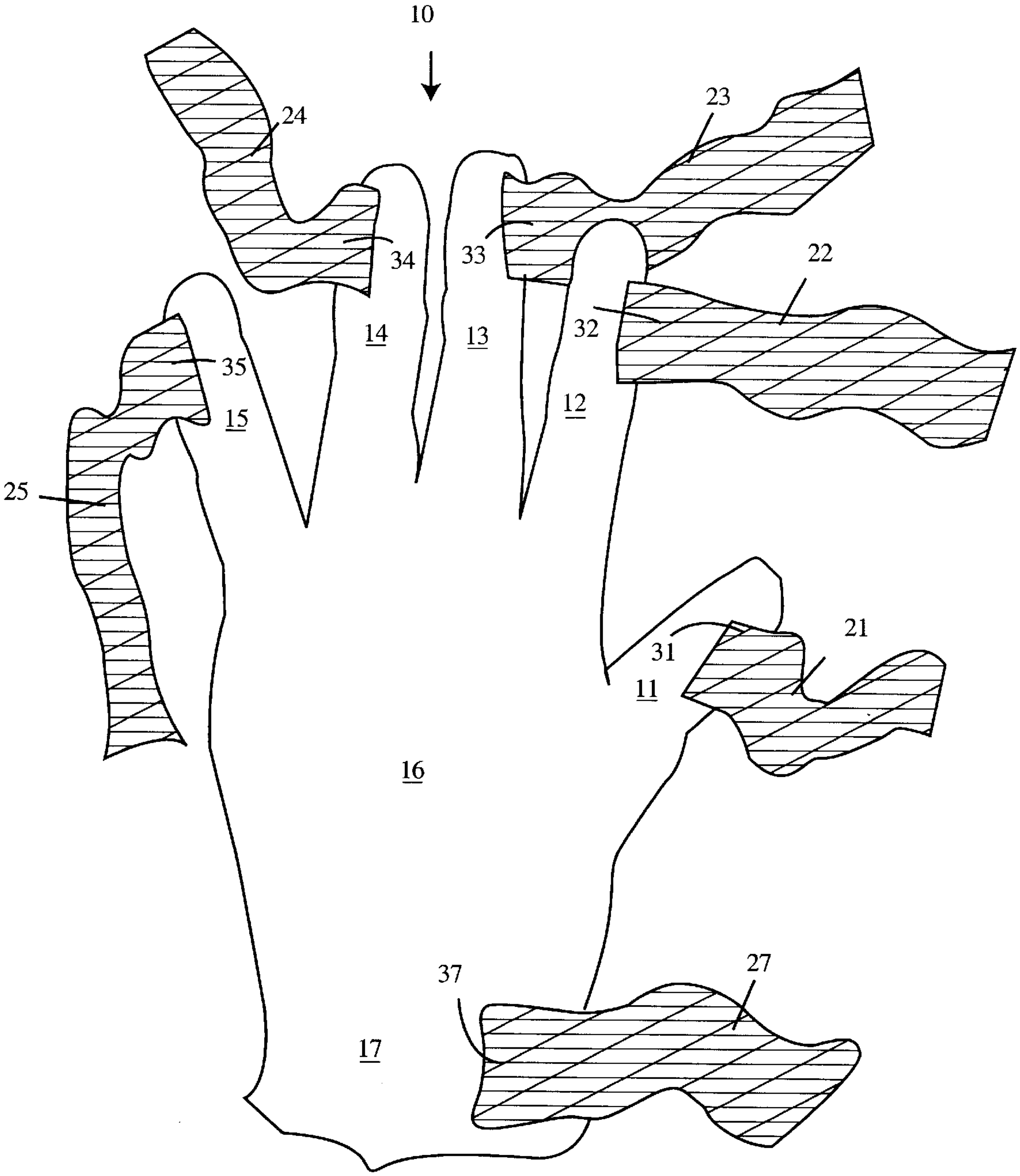
FIG. 1A shows a palm up view of a left hand of the hand over hand gloves of the invention.
Figure 1B:
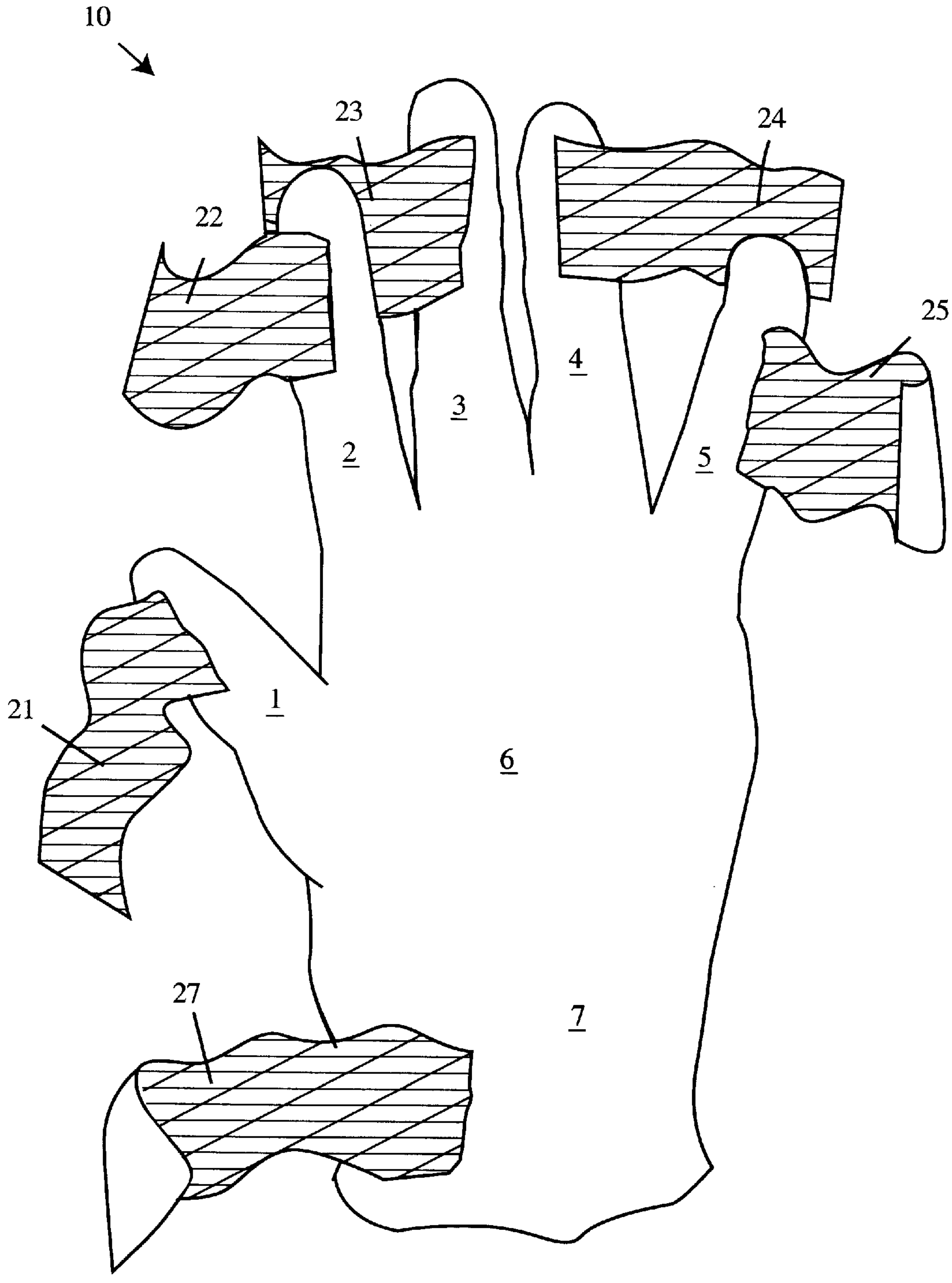
FIG. 1B shows a hand down view of the left hand glove of FIG 1A.

FIG. 1A shows a palm up view of a left hand 10 of the hand over hand gloves of the invention. FIG. 1B shows a hand down view of the left hand glove 10 of FIG. 1A. Referring to FIGS. 1A–1B, left hand glove 10 can be formed from a flexible material such as but not limited to latex, nylon, combinations thereof, and the like. Left hand glove 10 has a hand down portion with thumb portion 11, index finger 12, middle finger 13, fourth finger 14, pinkie finger 15, back dorsum portion 16, and back wrist portion 17. The palm up side has thumb portion 1, index portion 2, middle portion 3, fourth finger 4, and pinkie finger 5, palm portion 6 and front wrist portion 7. Fastener straps 21, 22, 23, 24, 25, and 27 can be made of flexible plastic material with self adhesive peelable layers on one side or both sides of each strap, and be approximately one inch wide by approximately six inches long. Alternatively, straps 21–25 and 27 can formed from flexible materials having hook and loop fasteners(i.e. Velcro®), and the like, on one or both sides of each strap. One end of each of straps 21, 22, 23, 24, 25, 27 can be attached to back dorsum portions 11, 12, 13, 14, 15, 17 of glove 10 at points 31, 32, 33, 34, 35, 37 by being sewn, adhered, and the like.

Figure 2A:
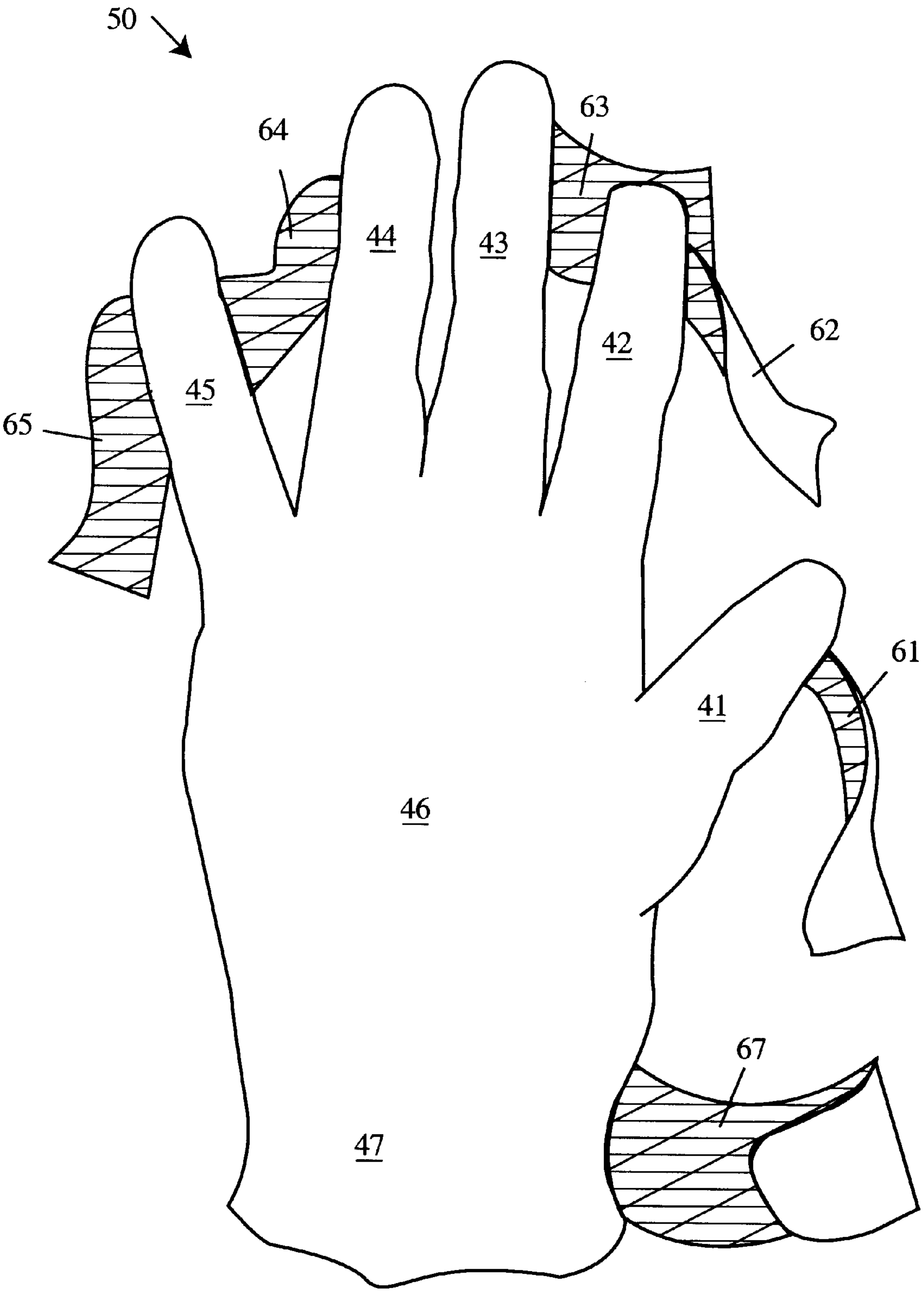
FIG. 2A shows a palm up view of a right hand of the hand over hand gloves of the invention.
Figure 2B:
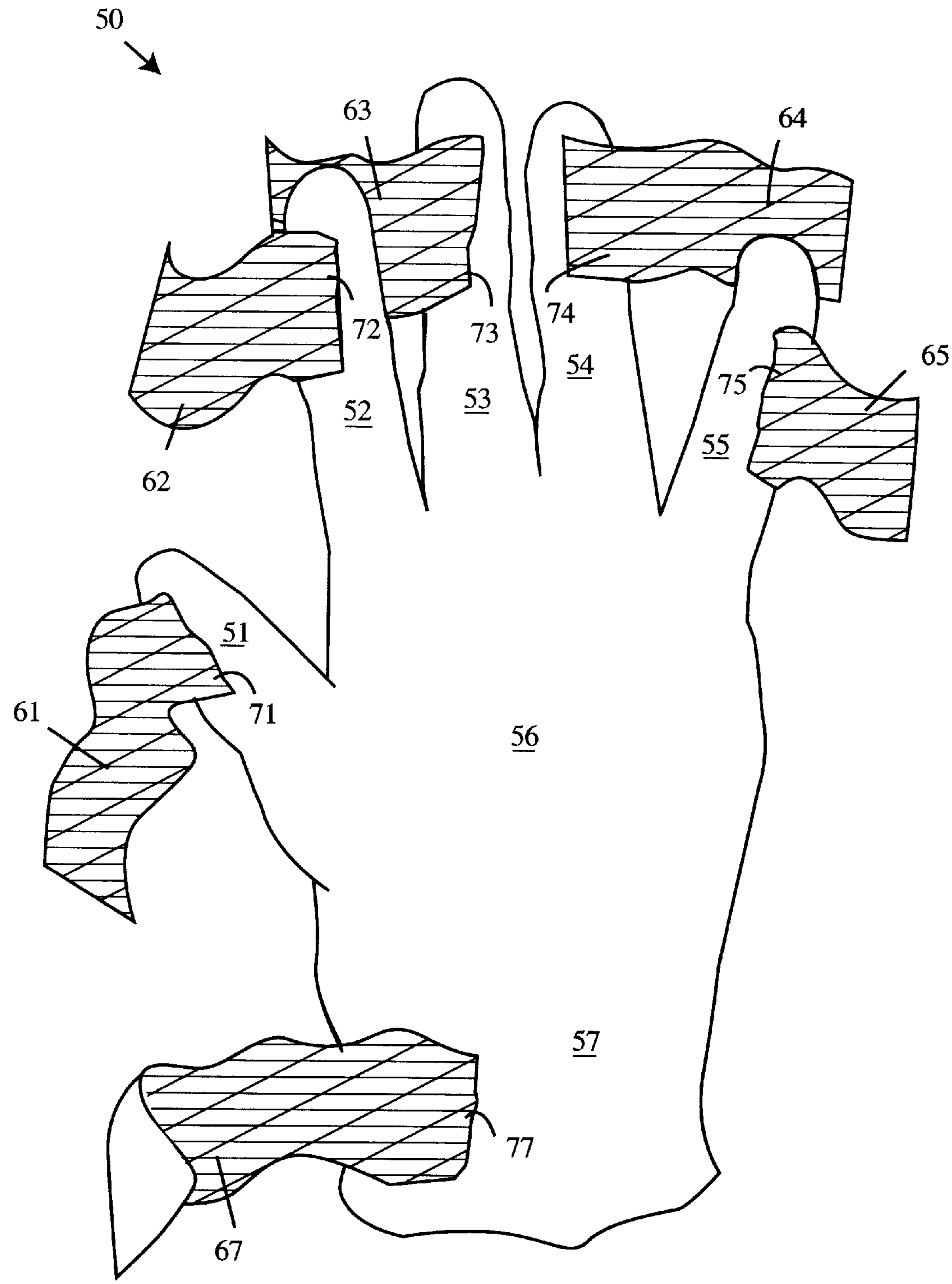
FIG. 2B shows a hand down view of the right hand glove of FIG. 2A.

FIG. 2A shows a palm up view of a right hand 50 of the hand over hand gloves of the invention. FIG. 2B shows a hand down view of the right hand glove 50 of FIG. 2A. Referring to FIGS. 2A–2B, right hand glove 50 can be formed from a flexible material such as but not limited to latex, nylon, combinations thereof, and the like. Right hand glove 50 has a hand down portion with thumb portion 51, index finger 52, middle finger 53, fourth finger 54, pinkie finger 55, back dorsum portion 56, and back wrist portion

57. The palm up side has thumb portion 41, index portion 42, middle portion 43, fourth finger 44, and pinkie finger 45, palm portion 46 and front wrist portion 47. Fastener straps 61, 62, 63, 64, 65, and 67 can be made of flexible plastic material with self adhesive peelable layers on one side or both sides of each strap, and be approximately one inch wide by approximately six inches long. Alternatively, straps 61–65 and 67 can formed from flexible materials having hook and loop fasteners(i.e. Velcro®), and the like, on one or both sides of each strap. One end of each of straps 61, 62, 63, 64, 65, 67 can be attached to back dorsum portions 51, 52, 53, 54, 55, 57 of glove 50 at points 71, 72, 73, 74, 75, 77 by being sewn, adhered, and the like.

Figure 3:
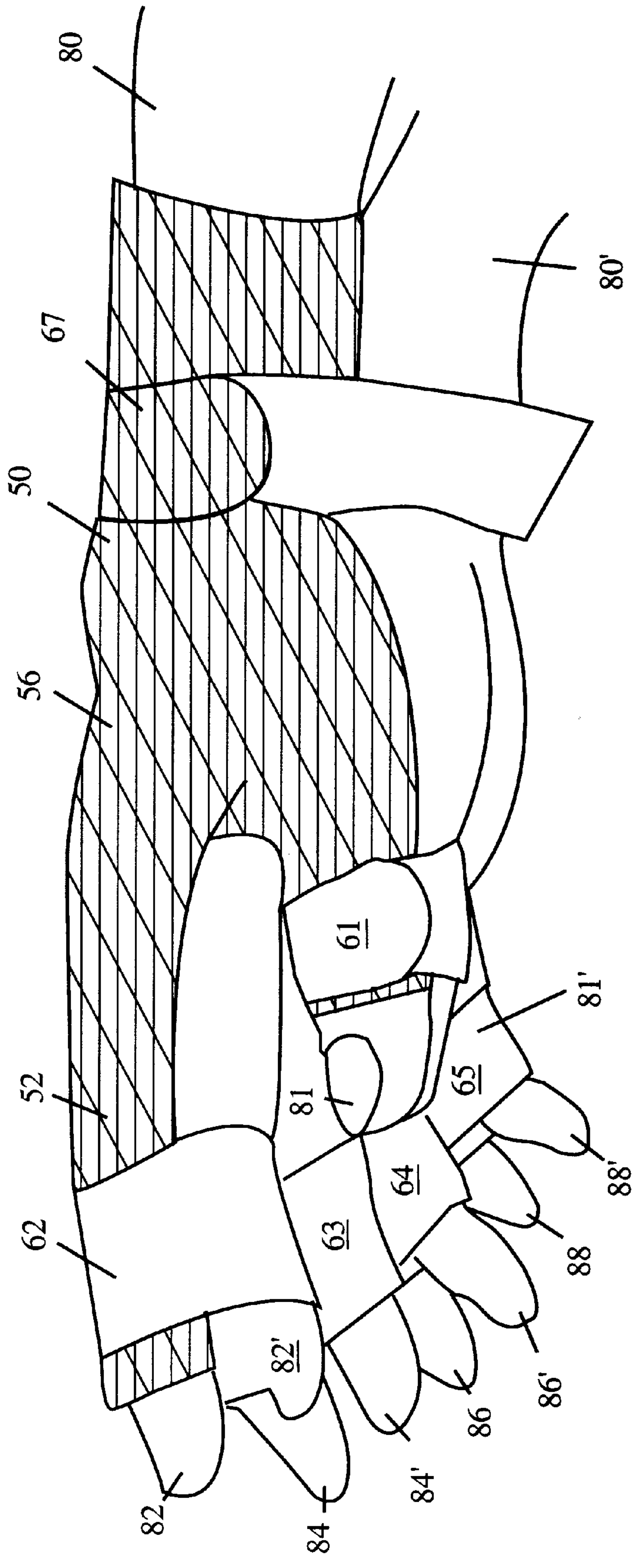
FIG. 3 is a view of the right hand glove of FIGS. 2A–2B being used with a therapist's hand and a patient's hand.

FIG. 3 is a view of the right hand glove 50 of FIGS. 2A–2B being used with a therapist's hand 80 and a patient's hand 80'. A palm surface of a therapist's hand lays in symmetry on top of the dorsum portion of the patient's affected hand. In FIG. 3, the right hand 80 of the therapist lays over the right hand 80' of the patient. Fastener strap 67 connects the wrist of the therapist to the patient. Fastener strap 61 connects the therapist's thumb 81 to the patient's thumb 81', strap 62 connects the therapists index finger 82 to the patient's index finger 82', strap 63 connects the therapist's middle finger 84 to the patient's middle finger 84', strap 64 connects the therapists fourth finger 86 to the patient's fourth finger 86', and strap 65 connects the therapists pinkie finger 88 to the patient's pinkie finger 88'.

Figure 4:
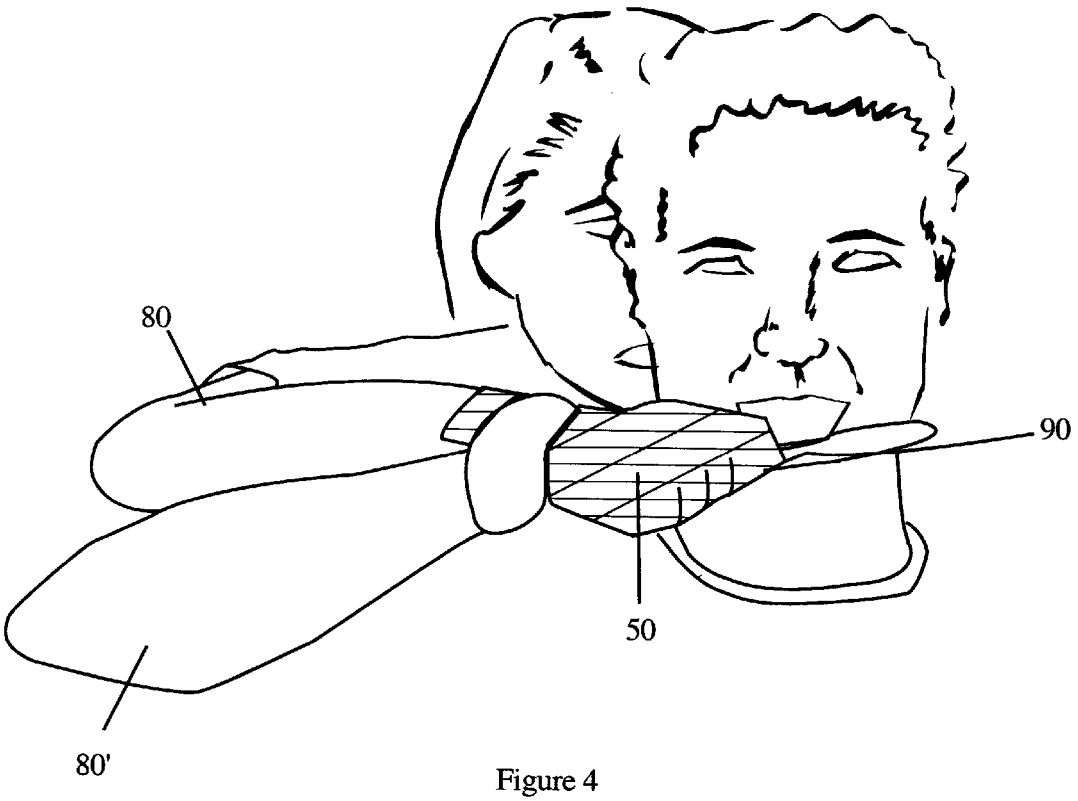
FIG. 4 is a view of the right hand glove with therapist's hand and patient's hand of FIG. 3 being applied to an rehabilitation task of brushing teeth.

FIG. 4 is a view of the right hand glove 50 with therapist's hand 80 and patient's hand 80' of FIG. 3 being applied to an rehabilitation/reeducation task of holding a tooth brush 90 for brushing teeth.

Figure 5:
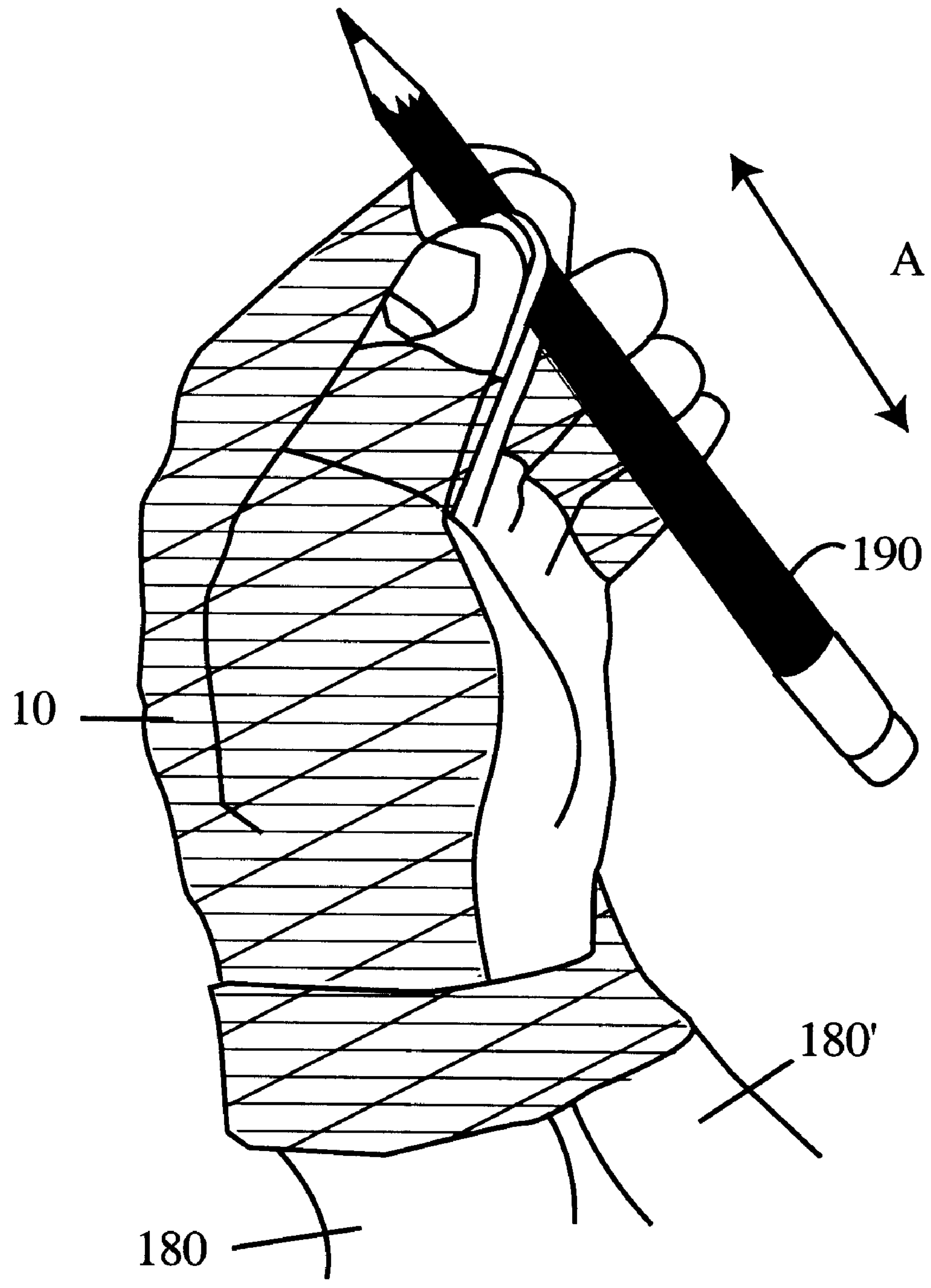
FIG. 5 is a view of the left hand glove of FIGS. 1A–1B being applied with the rehabilitation task of holding a pencil.

FIG. 5 is a view of the left hand glove 10 of FIGS. 1A–1B being applied with the rehabilitation/reeducation task of holding a pencil 190 and moving the pencil 190 backwards and forwards in the direction of arrow A.

Figure 6:
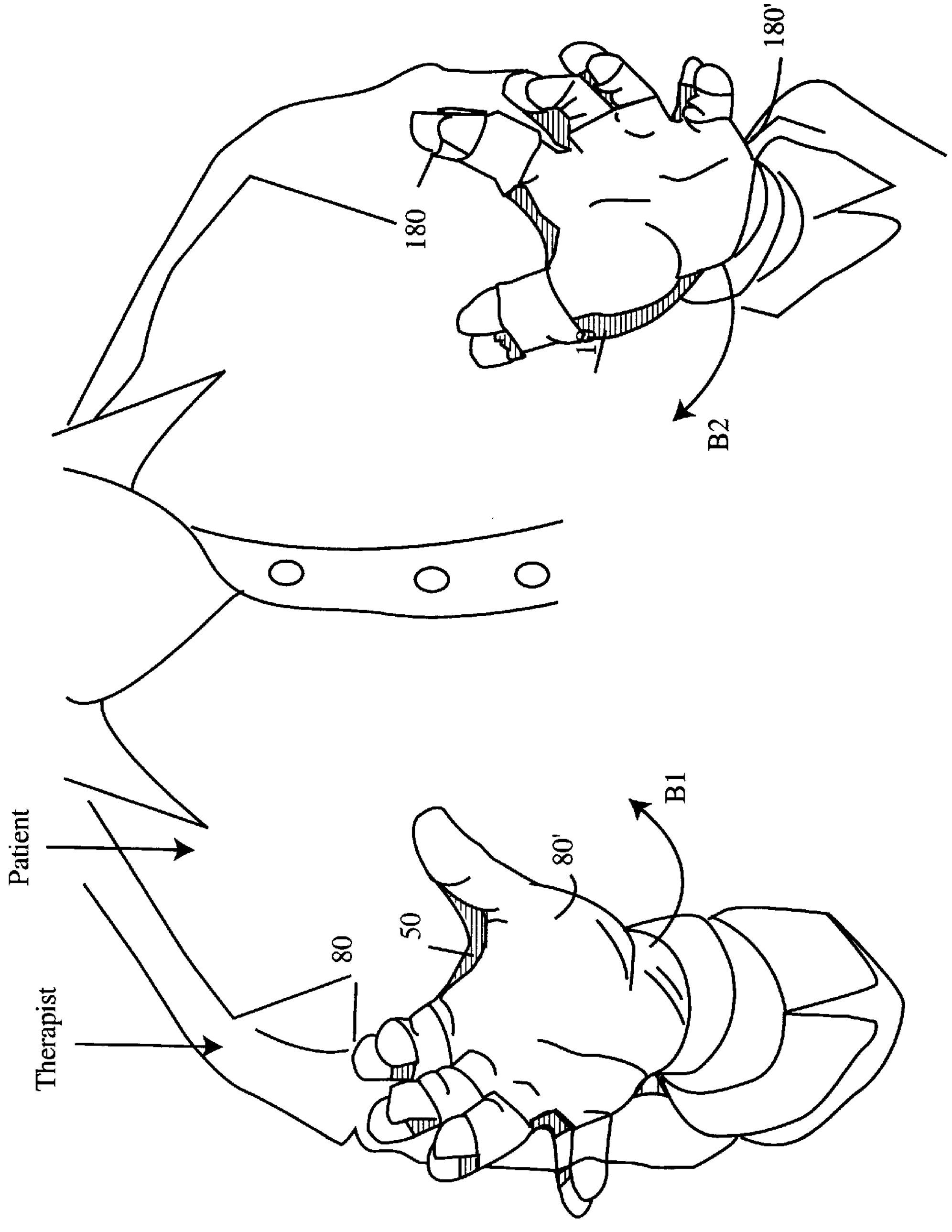
FIG. 6 is a view of the right hand glove and left hand glove of FIGS. 1A–2B, being used in an exercise function application.

FIG. 6 is a view of the right hand glove 50 and left hand glove 10 of FIGS. 1A–2B, being used in an exercise function application, where the therapist's right hand 80 and arm moves the patient's right hand 80' and arm in the rotatable direction of arrow B1, and the therapist's left hand 180 and arm moves the patient's left hand 180' in the rotatable direction of arrow B2.

Once the hand over hand gloves are being used, the therapist/aide can guide and control the patient's hands and movements including but not limited to reach, gross/refined grasp, fine pinch, in-hand manipulation, opposition type movements, functional object manipulation, and the like, in order to perform functional motor activities while allowing the patient to receive real and not simulated sensory inputs to their hands.

In addition to Cerebral Vascular Accidents(CVA) patients, and other neuralgic patients, the invention has applicability to other treatment populations, such as but not limited to pediatrics and geriatrics.

For pediatrics, the hand over hand invention can assist in developing proprioception and sensory/motor processing that is required for self-care and other functional developmental skills as well as increasing appropriate neuromuscular feedback to build on an overall system. The hand over hand method will develop upper extremity movement patterns, proper prehensile development and refinement of manipulative skills such as but not limited to pincer grasp, writing grasp and various functional grasps.

The novel hand over hand method eliminates the need for the child to imitate movements which involve a lot of higher level functioning. Visual imitation generally has required 1) receiving accurate visual input, 2) transferring messages to the brain and down appropriate neuralgic pathways, and 3) which results in motor output. These complex systems of visual imitation are, slow to develop, particularly in developmentally delayed individuals. Fails attempts at learning new tasks serves to negate any reinforcement to continue practicing skills. Continuous repetition of movements serves as the most effective motor learning strategy.

With the hand over hand invention, movement patterns are automatically assimilated with functional activities. This connection will develop and strengthen sensory and motor connections at a neuralgic level. Successful precise movement patterns while associated within a meaningful context will allow the child to associate more positive feelings with the respective skills resulting in increasing the willingness to continue to practice and participate.

For geriatrics, activities of daily living(ADL) requires constant retraining due to normal physical/cognitive/perceptual declines. Here the patient has deviated somewhat from their normal functional routines. Using the hand over hand invention provides a continuous refined technique of practicing automatic skills within a safe environment.

Second Embodiment

Figure 7A:
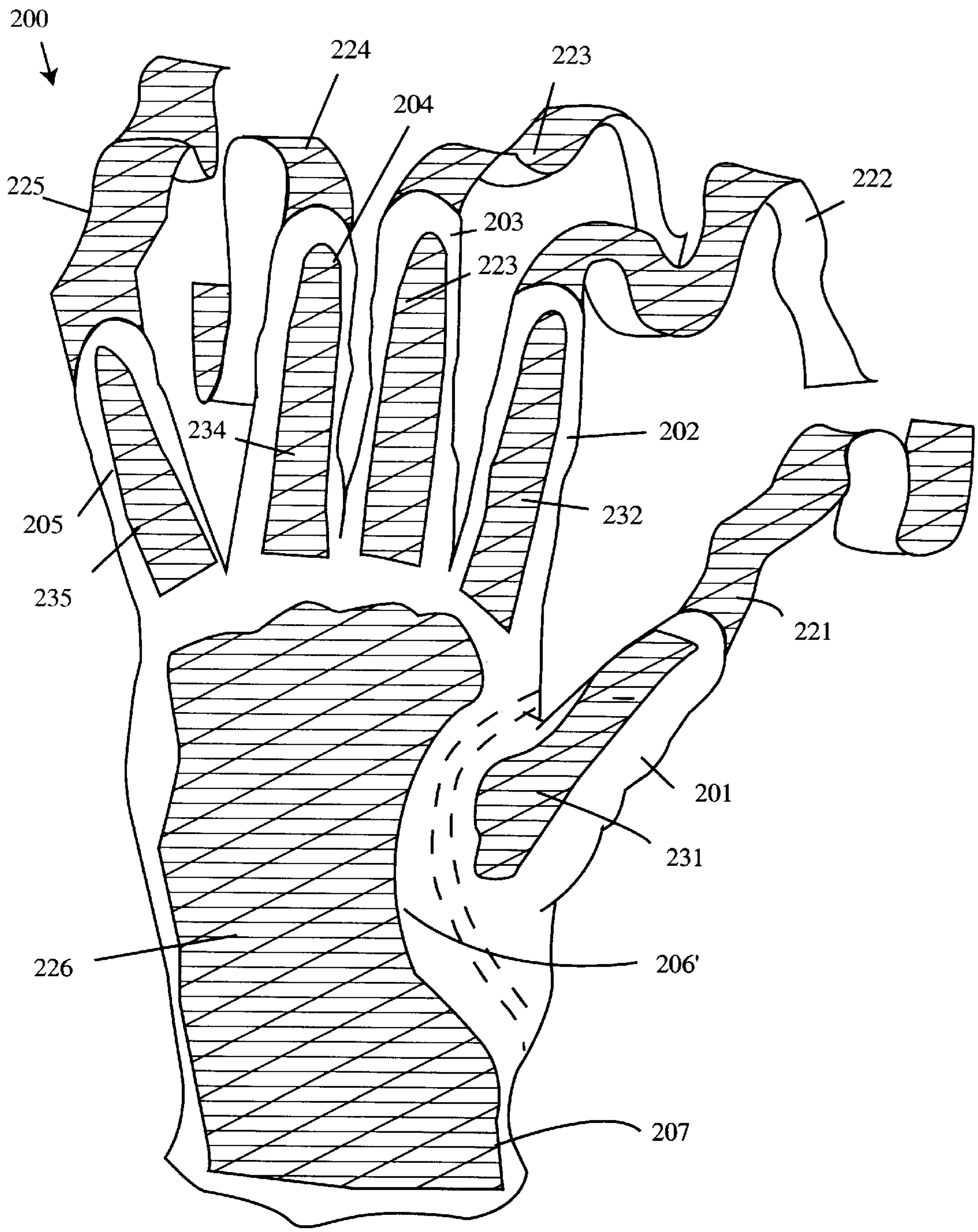
FIG. 7A is a palm view a right hand grasp assistance glove of the invention.
Figure 7B:
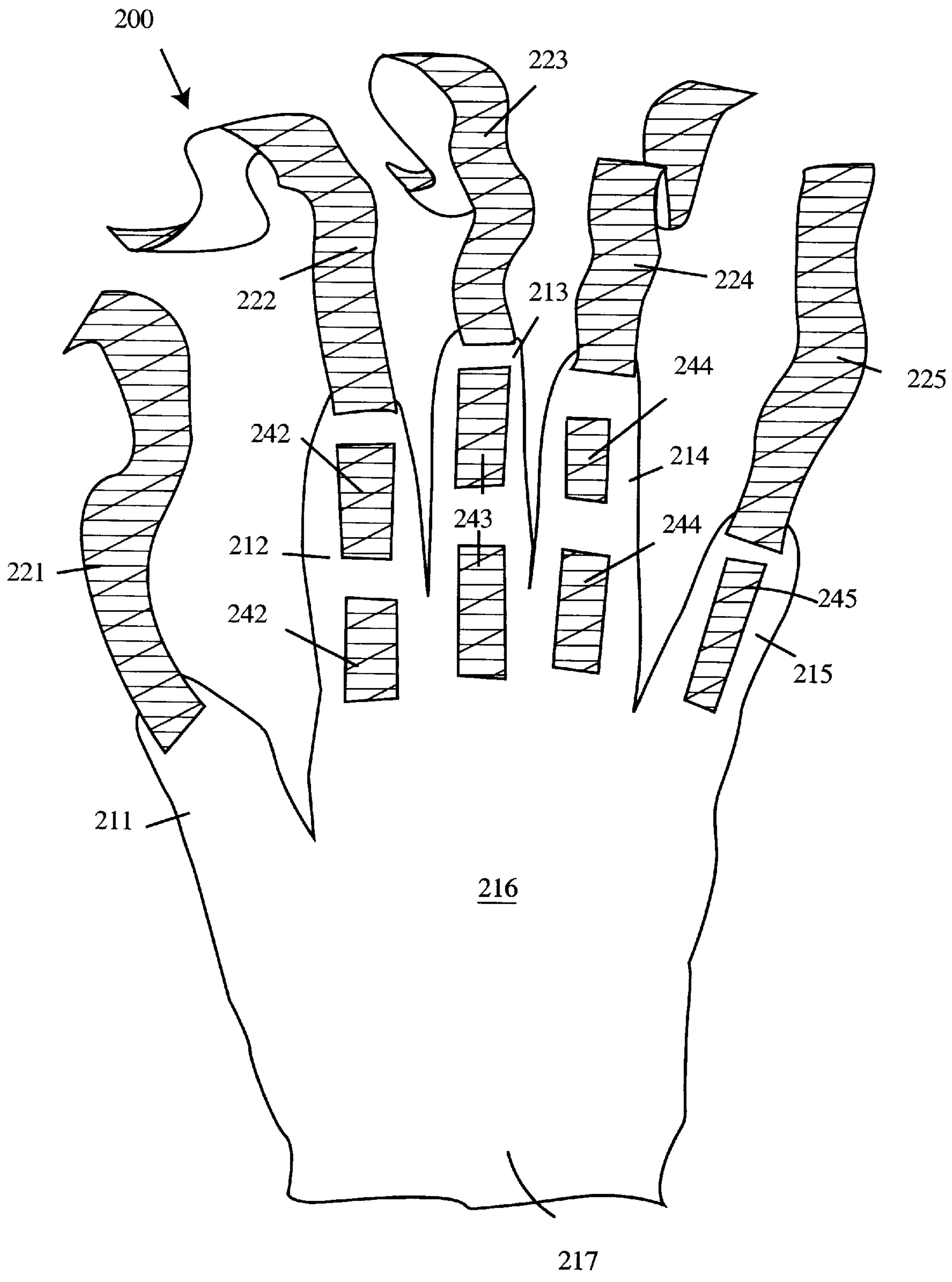
FIG. 7B is a dorsum view of the right hand grasp assistance glove of FIG. 7A.

FIG. 7A is a palm view a right hand grasp assistance glove 200 of the invention. FIG. 7B is a dorsum view of the right hand grasp assistance glove 200 of FIG. 7A. Referring to FIGS. 7A–7B, right hand grasp assistance glove 200 can be formed from flexible material such as but not limited to latex, nylon, combinations thereof, and the like. Referring to FIG. 7A, glove 200 can have palm portion side 206, front wrist portion 207 with thumb 201, index finger 202, middle finger 203, fourth finger 204, and pinkie finger 205. Attached to palm portion 206 can be a fastener pad 226, attached to palm side of thumb 201 can be a palm thumb pad 231, attached to the palm side of index finger 202 can be a palm index fastener pad 232, attached to the palm side of middle finger 203 can be a palm middle fastener pad 233, attached to the palm side of fourth finger 204 can be a palm fourth finger pad 234, and attached to the palm side of pinkie finger 205 can be a palm pinkie pad 235.

Referring to FIG. 7B, the dorsum side 216 of glove 100 has a wrist portion 217, thumb 211, index finger 212, middle finger 213, fourth finger 214, pinkie finger 215. Attached to the dorsum side of index finger 212 can be dual fastener strips 242, attached to the dorsum side of middle finger 213 can be dual fastener strips 243, attached to the dorsum side of fourth finger 214 can be dual fastener strips 244, and attached to the dorsum side of pinkie finger 215 can be fastener strip 245. Extending outward from the tip ends of each of the five fingers can be approximately four inch long by approxately half inch wide fastener straps 221, 222, 223, 224, and 225.

The fastener pads, strips and straps used in FIGS. 7A–7B can have surfaces with hook and loop fasteners such as Velcro®, and the like. Alternatively, the fastener pads, strips, and straps can be formed from self adhesive peel and stick tape, and the like. The fastener pads, strips and straps can be adhered to the surfaces of the glove 200 by being sewn thereon, adhered, and the like. The fastener pads, straps, and strips can be formed from the materials described in the first embodiment.

Figure 8A:
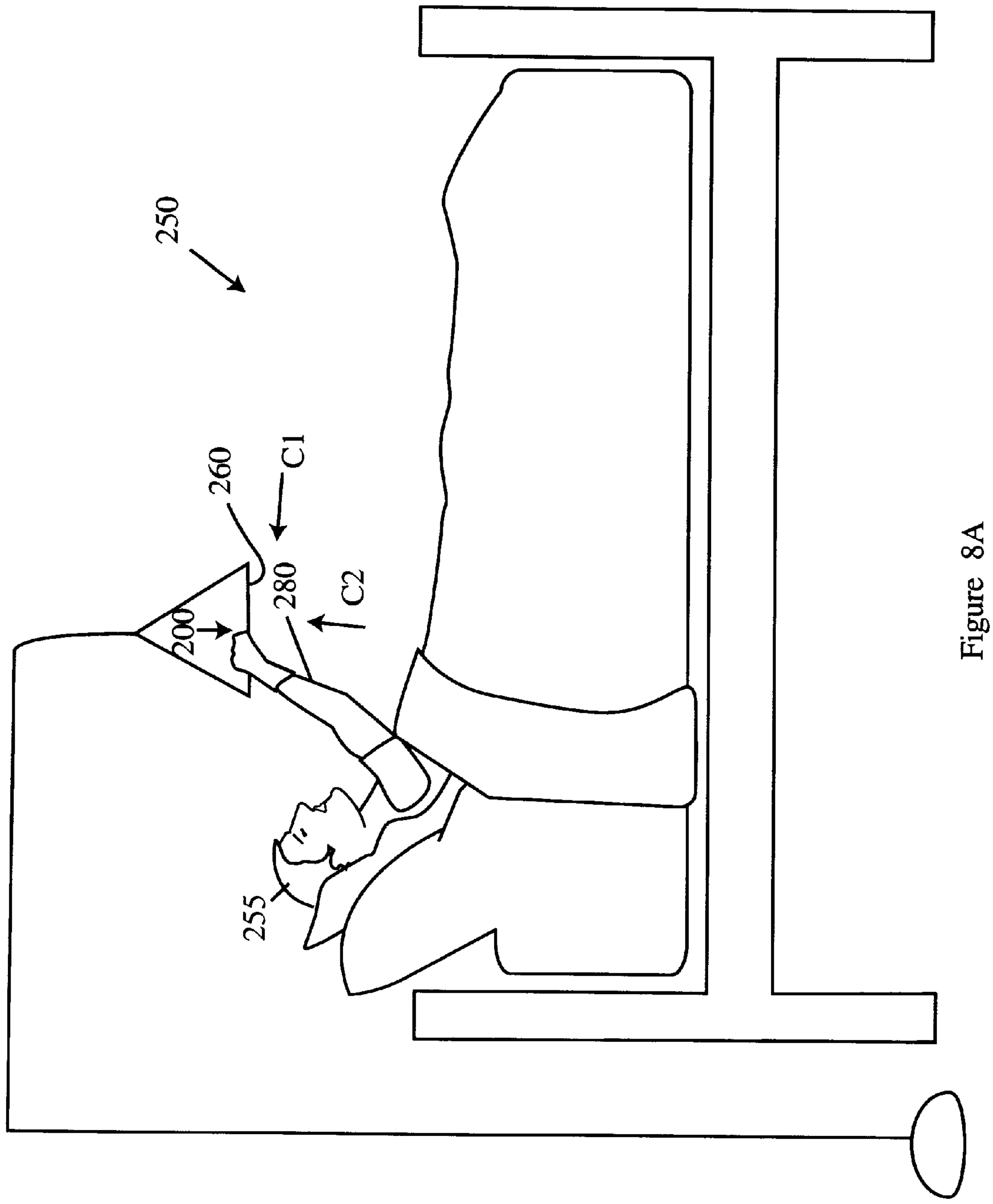
FIG. 8A is a perspective view of the right hand grasp assistance glove of FIGS. 7A–7B in application.
Figure 8B:
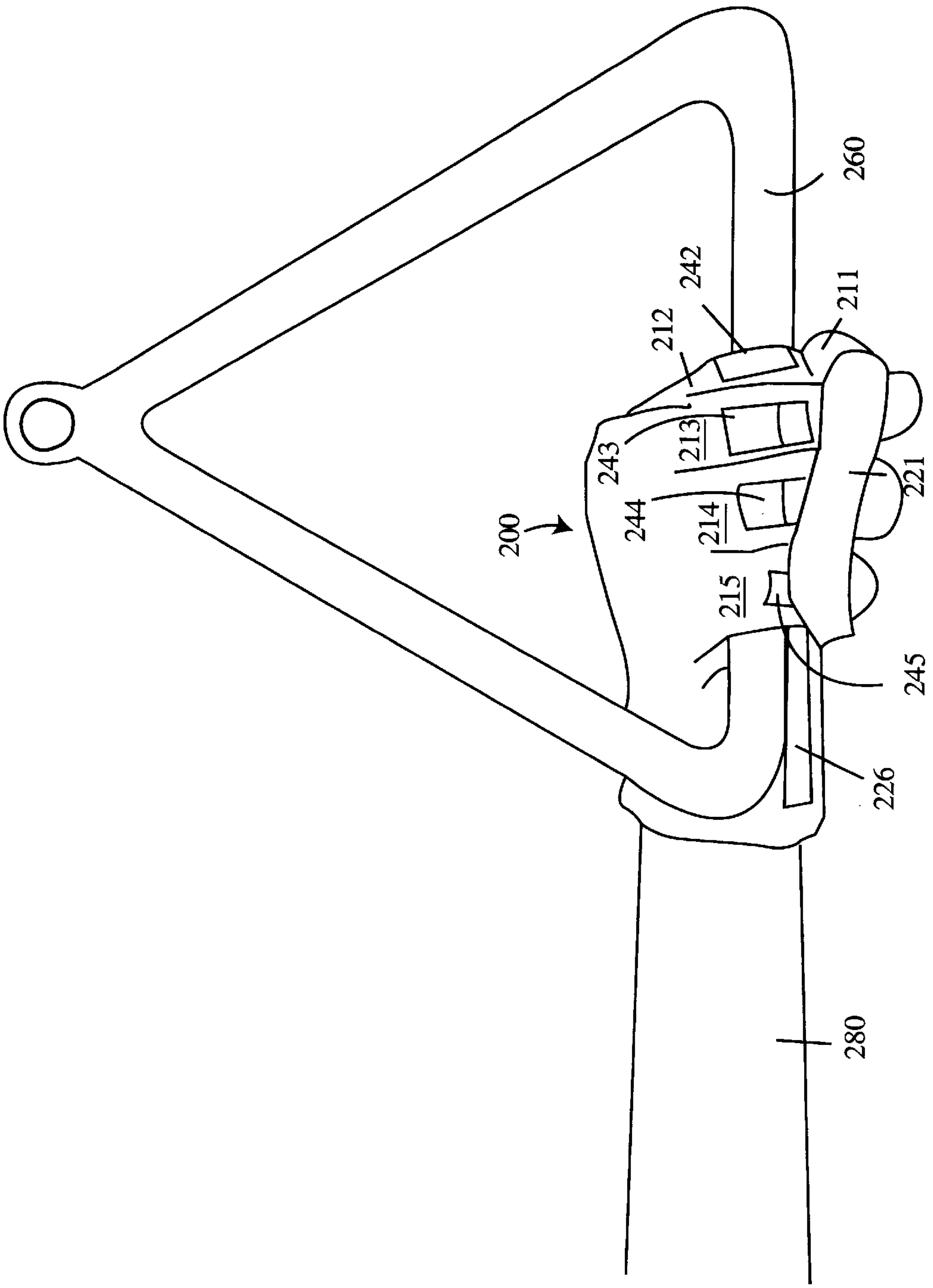
FIG. 8B is an enlarged front view of the grasp assistance glove of FIG. 8A along arrow C1.
Figure 8C:
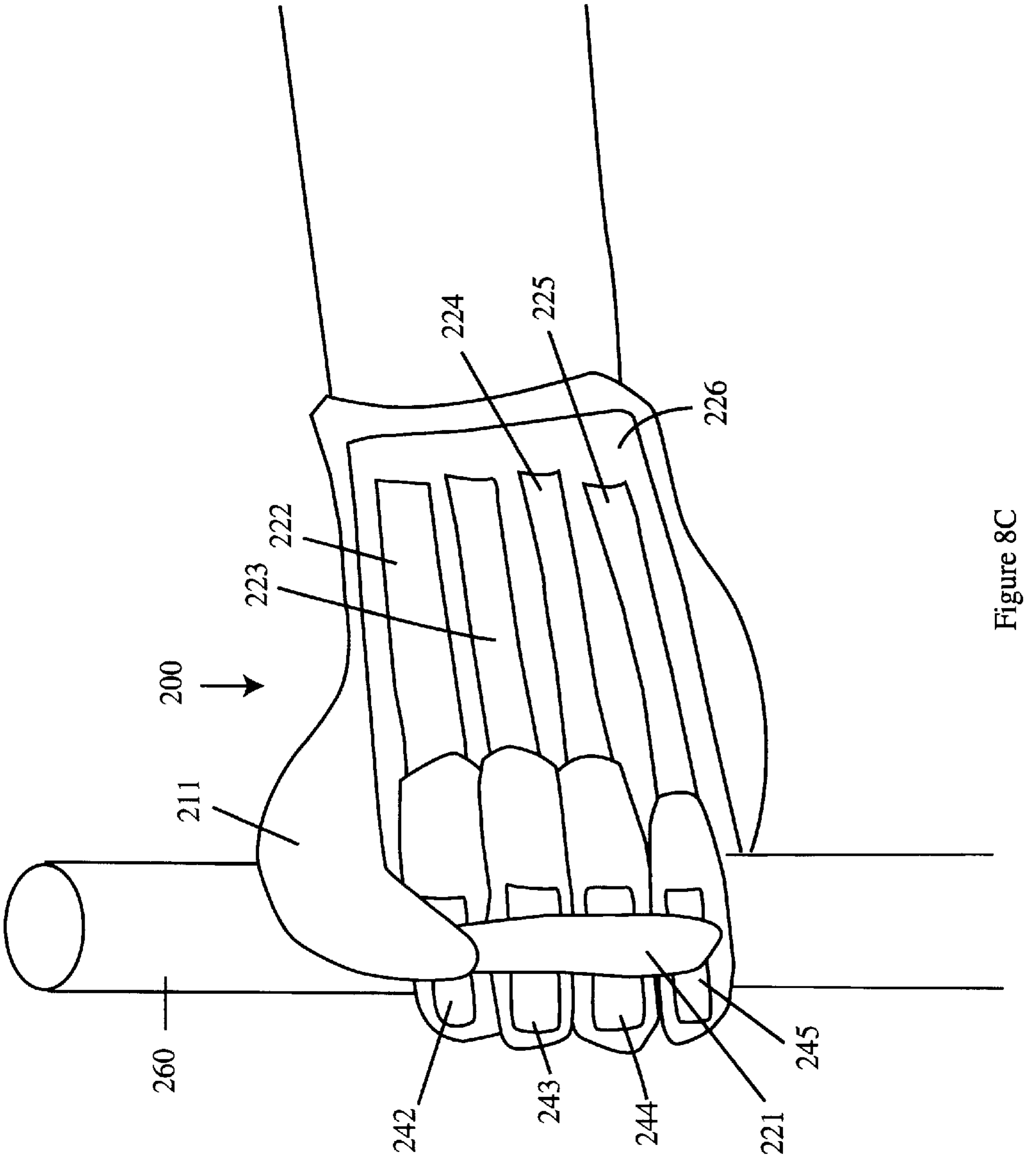
FIG. 8C is a bottom view of the grasp assistance glove of FIG. 8A along arrow C2.

FIG. 8A is a perspective view 250 of the right hand grasp assistance glove 200 of FIGS. 7A–7B in application with a bedridden patient 255 using their right hand 280 using the right grasp assistance glove 200 to grab an exercise bar 260. FIG. 8B is an enlarged front view of the grasp assistance glove 200 of FIG. 8A along arrow C1. FIG. 8C is a bottom view of the grasp assistance glove 200 of FIG. 8A along arrow C2. Referring to FIGS. 8A–8C, thumb fastener strap 221 can attach to index finger fastener strip 242, middle finger fastener strip 243, fourth finger fastener strip 244 and pinkie finger fastener strip 245. Fastener straps 222, 223, 224, 225, and 226 can attach to palm fastener pad 226.

Figure 9:
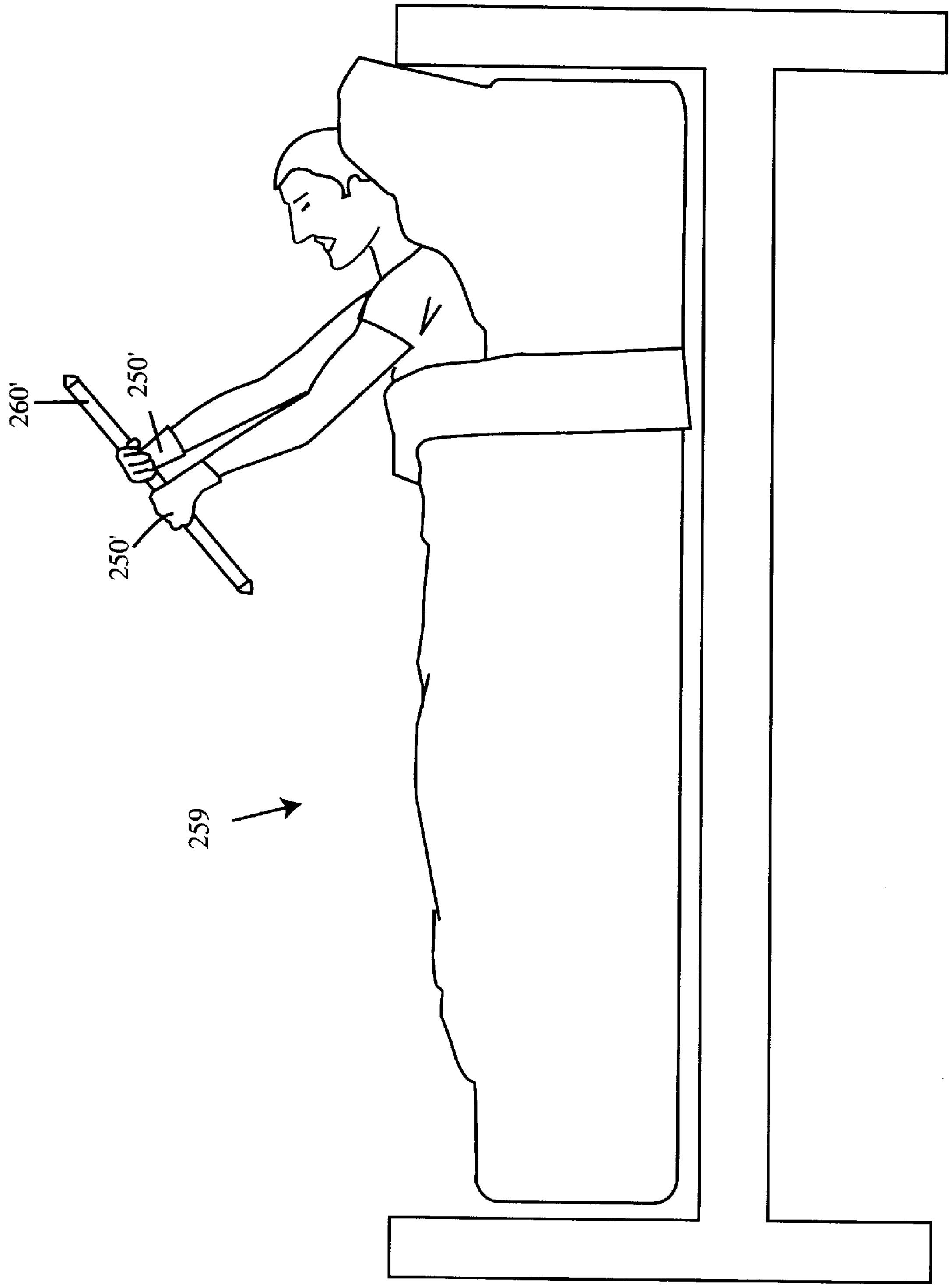
FIG. 9 is a perspective view of using a right and left hand grasp assistance gloves.

FIG. 9 is a perspective view of using a right and left hand grasp assistance gloves 250 and 250' grabbing another exercise bar 260'. The grasp assistance gloves allows patients to maintain a functional grasp during various rehabilitation and reeducation exercises.

Third Embodiment

Figure 10:
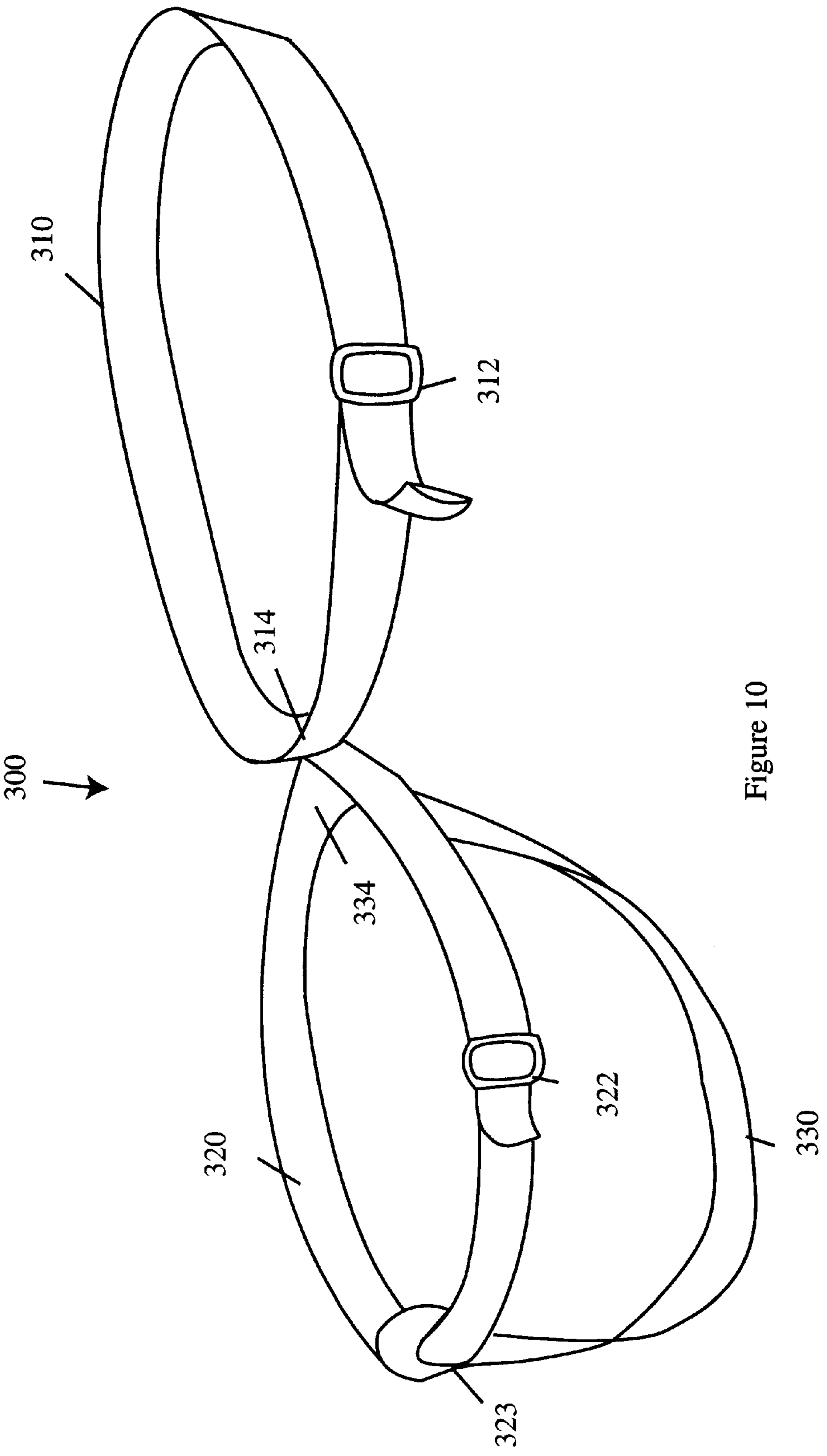
FIG. 10 is a perspective view of a harness system used for rehabilitation and reeducation exercises.
Figure 11:
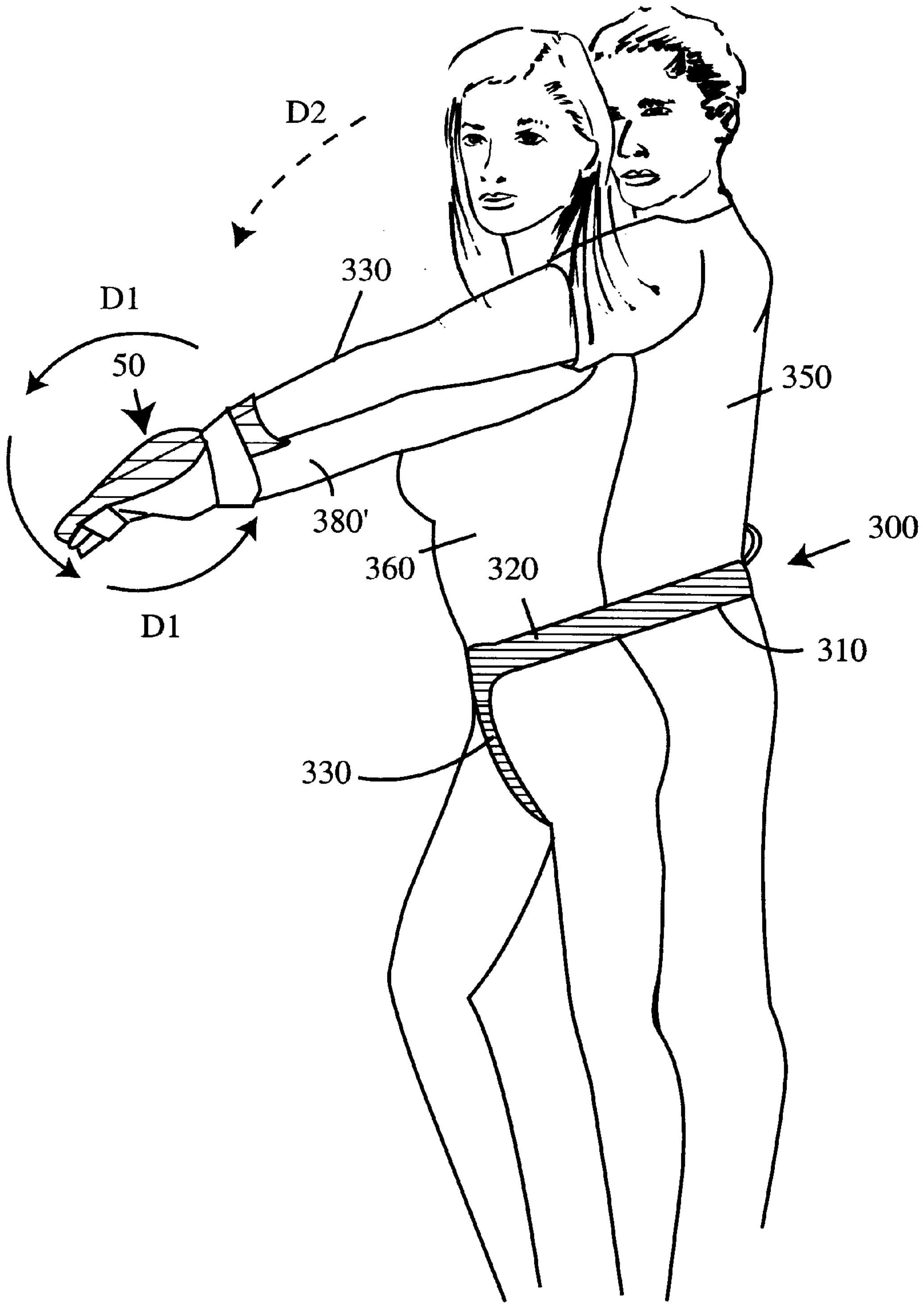
FIG. 11 shows the harness of FIG. 10 with the hand over hand system of the first embodiment.

FIG. 10 is a perspective view of a harness system 300 used for rehabilitation and reeducation exercises. FIG. 11 shows the harness 300 of FIG. 10 with the hand over hand system of the first embodiment. Harness 300 can include a therapist belt portion 310 having a width adjustable belt clasp fastener 312. Connected to one end 314 of belt portion 310 is a patient belt portion 320 having a width adjustable belt clasp fastener 322. A lower belt portion 330 attaches at points 332 and 334 to upper belt portion 320 for use with connecting the harness 300 between the legs of the patient. Harness 300 can be formed from flexible materials such as but not limited to leather, canvass, nylon, plastic, combinations, thereof, and the like. A therapist 350 wearing belt portion 310 faces the back of a patient 360 in order to allow the patient 360 to do standing rehabilitation and reeducation exercises such as circular motion D1 and bending motion D2. The harness 300 can be used with the hand 380 over hand 380' gloves 10, 50 shown in the first embodiment. The harness 300 allows the therapist 350 to use their body to support the patient 360 safely if balance and stability is compromised, and helps alleviate the patient's fear of falling. Although FIG. 11 shows the harness being used with the hand over hand gloves, the harness 300 can be used separately for exercises. Additionally, instead of a therapist, the harness can also be secured to a stationary object such as a support pillar, a door, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A hand over hand system for exercising hands, fingers and arms for rehabilitation and reeducation, comprising in combination:

a first glove, having first fasteners adapted to be worn on a first hand of a first person, wherein a palm surface of the first hand is laid in symmetry on top of a dorsum of a corresponding hand of a second person and the first fasteners attach to the first corresponding hand for rehabilitation and reeducation exercises; and a harness having a first belt and a second belt adapted for attaching a waist portion of the first person to a waist portion of the second person, wherein the harness increases safety and decreases patient fear while the second person is doing standing rehabilitation and reeducation exercises.

2. The hand over hand system of claim 1, wherein the first and second belt includes:

a portion for passing between the legs of the second person.

3. The hand over hand system of claim 1, wherein the first and second belt includes:

hook and loop fasteners.

4. The hand over hand system of claim 1, wherein the first and second belt includes:

self adhesive tape fasteners.

5. The hand over hand system of claim 1, wherein the first and second belt includes:

belt clasp fasteners.

6. A hand over hand and waist to waist exercise system, comprising in combination:

first fastener means adapted for connecting a portion of a first hand of a first person to a second hand of a second person; and second fastener means adapted for connecting a portion of a first waist of a first person to a second waist of a second person, wherein the first person can exercise the portion of the second hand and the portion of the second waist of the second person.

7. The hand over hand and waist to waist exercise system of claim 6, wherein the first fastener means includes:

at least one strap adapted for connecting at least one finger of the first hand to one finger of the second hand.

8. The hand over hand and waist to waist exercise system of claim 6, wherein the first fastener means includes:

a glove for connecting at least one finger of the first hand to one finger of the second hand.

9. The hand over hand and waist to waist exercise system of claim 6, wherein the second fastener means includes:

a belt for connecting the portion of the first waist to the portion of the second waist.

10. The hand over hand and waist to waist exercise system of claim 6, wherein the second fastener means includes:

a harness for connecting the portion of the first waist to the portion of the second waist.

11. A method for using an exercising system, comprising the steps of:

securely attaching a first fastener about at least one finger of a first user to about at least one finger of a second user; and securely attaching a second fastener to a waist portion of the first user and a waist portion of the second user, wherein the first fastener and second fastener are used by the first user for exercising the at least one finger and the waist portion of the second user.

12. The method of using an exercising system of claim 11, wherein the securing of the first fastener includes:

securely attaching a strap to the least one finger of the first user and to the at least one finger of the second user.

13. The method of using an exercising system of claim 11, wherein the securing of the first fastener includes:

securely attaching a glove to the least one finger of the first user and to the at least one finger of the second user.

14. The method of using an exercising system of claim 11, wherein the securing of the second fastener includes:

securely attaching a belt to the portion of the waist of the first user and to the portion of the waist of the second user.

15. The method of using an exercising system of claim 11, wherein the securing of the second fastener includes:

securely attaching a harness to the portion of the waist of the first user and to the portion of the waist of the second user.

16. A method of exercising fingers of a hand of one person by the fingers of a hand of another person using an exercising system, comprising the steps of:

securely attaching a first fastener about one finger of a first user to overlay and attach to one finger of a second user;

securely attaching a second fastener about another finger of the first user to overlay and attach to another finger of the second user, the first fastener being separate from the second fastener;

manipulating the one finger of the second user solely with the first fastener and the one finger of the first user; and manipulating the another finger of the second user solely with the second fastener and the another finger of the first user, wherein the first fastener and the second fastener allows for at least two fingers of the first hand to perform individual and separate manipulations of at least two fingers of the second hand.

17. The method of exercising of claim 16, wherein thumbs of the first user and the second user are securely attached to the first fastener, and forefingers of the first user and the second user are securely attached to the second fastener.

* * * * *